(12) United States Patent
Thompson

(10) Patent No.: US 11,898,184 B2
(45) Date of Patent: Feb. 13, 2024

(54) LOW GLYCEMIC SUGAR COMPOSITION

(71) Applicant: SWEET SENSE INC., Bethesda, MD (US)

(72) Inventor: Daryl Thompson, Winter Haven, FL (US)

(73) Assignee: SWEET SENSE INC., Bethesda, MD (US)

( * ) Notice: Subject to any disclaimer, the term of this patent is extended or adjusted under 35 U.S.C. 154(b) by 0 days.

(21) Appl. No.: 15/698,159

(22) Filed: Sep. 7, 2017

(65) Prior Publication Data
US 2019/0071703 A1 Mar. 7, 2019

(51) Int. Cl.
| | | |
|---|---|---|
| C12P 19/12 | (2006.01) | |
| C13K 1/00 | (2006.01) | |
| C13K 11/00 | (2006.01) | |
| C07C 35/16 | (2006.01) | |
| A23L 29/30 | (2016.01) | |
| C13K 13/00 | (2006.01) | |
| A61P 3/10 | (2006.01) | |
| A23L 33/125 | (2016.01) | |
| A61K 31/7016 | (2006.01) | |
| A61K 31/047 | (2006.01) | |

(52) U.S. Cl.
CPC ............ *C12P 19/12* (2013.01); *A23L 29/30* (2016.08); *A23L 33/125* (2016.08); *A61K 31/047* (2013.01); *A61K 31/7016* (2013.01); *A61P 3/10* (2018.01); *C07C 35/16* (2013.01); *C13K 1/00* (2013.01); *C13K 11/00* (2013.01); *C13K 13/00* (2013.01); *A23V 2002/00* (2013.01)

(58) Field of Classification Search
CPC ......... C07C 35/16; C12P 19/12; C13K 11/00; C13K 1/00; A61K 31/045; A23L 2/60
USPC .......................................................... 514/53
See application file for complete search history.

(56) References Cited

U.S. PATENT DOCUMENTS

| | | | | |
|---|---|---|---|---|
| 3,107,605 A * | 10/1963 | Barry, I | .................. | C13B 10/04 100/75 |
| 4,465,698 A * | 8/1984 | Bussiere | .................. | A23B 7/08 127/38 |
| 4,786,722 A | 11/1988 | Zehner | | |
| 4,921,877 A | 5/1990 | Cashmere et al. | | |
| 5,124,360 A | 6/1992 | Larner et al. | | |
| 5,656,094 A * | 8/1997 | Peckous | .................. | C13K 1/10 127/46.1 |
| 5,763,392 A * | 6/1998 | Hansen | ................ | A61K 31/047 514/6.9 |
| 5,776,887 A | 7/1998 | Wilbert et al. | | |
| 5,902,797 A | 5/1999 | Bell et al. | | |
| 5,968,896 A | 10/1999 | Bell et al. | | |
| 6,039,985 A | 3/2000 | Kamarei | | |
| 6,194,009 B1 | 2/2001 | Kamarel | | |
| 6,248,375 B1 * | 6/2001 | Gilles | ..................... | A23L 33/40 426/72 |
| 6,294,520 B1 | 9/2001 | Naito | | |
| 6,432,464 B1 | 8/2002 | Andersen et al. | | |
| 6,492,339 B1 | 12/2002 | Sleevi et al. | | |
| 6,663,780 B2 * | 12/2003 | Heikkila | .............. | B01D 15/185 127/46.2 |
| 6,774,111 B1 | 8/2004 | Wolf et al. | | |
| 6,946,451 B2 | 9/2005 | Takada et al. | | |
| 7,993,687 B2 * | 8/2011 | Kawa | ..................... | A61K 36/70 424/725 |
| 8,071,145 B2 | 12/2011 | Dewille et al. | | |
| 8,148,350 B2 | 4/2012 | Van Laere et al. | | |
| 8,377,430 B2 | 2/2013 | Donnet-Hughes et al. | | |
| 8,414,706 B2 | 4/2013 | Foraci | | |
| 8,512,739 B2 | 8/2013 | Carlson et al. | | |
| 8,642,110 B2 | 2/2014 | Abrahamse et al. | | |
| 8,709,521 B2 | 4/2014 | Prakash et al. | | |
| 9,060,536 B2 | 6/2015 | Hansen et al. | | |
| 9,234,023 B2 | 1/2016 | Bilsky et al. | | |
| 9,247,763 B2 | 2/2016 | Bouritius et al. | | |
| 9,259,410 B2 | 2/2016 | Lamensdorf et al. | | |
| 10,314,853 B2 | 6/2019 | Von Maltzahn et al. | | |
| 10,525,016 B2 | 1/2020 | Kuang et al. | | |
| 10,752,888 B2 | 8/2020 | Yang et al. | | |
| 2001/0039297 A1 | 11/2001 | Allan | | |
| 2004/0127460 A1 | 7/2004 | Wolf | | |

(Continued)

FOREIGN PATENT DOCUMENTS

| | | |
|---|---|---|
| CN | 107348288 | 11/2017 |
| CN | 107466860 | 12/2017 |

(Continued)

OTHER PUBLICATIONS

Kalac, (J. Of the Sci. Food and Agric., 2013, 93, 209-218.*

(Continued)

*Primary Examiner* — Yih-Horng Shiao

(74) *Attorney, Agent, or Firm* — Stephen J. Weyer, Esq.; Stites & Harbison, PLLC

(57) ABSTRACT

A composition includes a sugar source and inositol. The sugar source is one more sugars select from the group consisting of glucose, sucrose, sucrolose, tagatose, galactose, high fructose corn syrup, fructose, isoglucose, and rhamnose. The composition of sugar and inositol has an unique properties that prevents or limits the signaling of TNF-α and associated pro-inflammatory cytokines when metabolized by an individual consuming the composition. Accordingly, the composition can be advantageously used to control blood glucose levels, treat diabetes and related conditions as well as treat diseases based on an inflammatory response.

26 Claims, No Drawings

(56) References Cited

U.S. PATENT DOCUMENTS

| | | | |
|---|---|---|---|
| 2006/0058243 | A1 | 3/2006 | Chen et al. |
| 2007/0116800 | A1* | 5/2007 | Prakash .................. A23G 4/10 |
| | | | 426/3 |
| 2008/0107787 | A1 | 5/2008 | Prakash et al. |
| 2008/0108548 | A1* | 5/2008 | Luyer ..................... A61P 43/00 |
| | | | 424/439 |
| 2009/0004220 | A1 | 1/2009 | McAnalley et al. |
| 2009/0176741 | A1 | 6/2009 | Nieuwenhuis et al. |
| 2010/0285201 | A1 | 11/2010 | Catani et al. |
| 2011/0086924 | A1 | 4/2011 | Okazaki et al. |
| 2011/0224311 | A1 | 9/2011 | Palmer et al. |
| 2011/0236551 | A1 | 9/2011 | Hammond et al. |
| 2011/0318468 | A1 | 12/2011 | Kakhaberi et al. |
| 2012/0190643 | A1 | 7/2012 | Van Laere et al. |
| 2013/0136836 | A1 | 5/2013 | Putter et al. |
| 2014/0004083 | A1* | 1/2014 | Hollard ................. A01N 1/0221 |
| | | | 424/93.4 |
| 2014/0010870 | A1 | 1/2014 | Unfer |
| 2014/0093586 | A1 | 4/2014 | Dolhun |
| 2014/0242255 | A1 | 8/2014 | Jia et al. |
| 2015/0018316 | A1 | 1/2015 | Jennings |
| 2015/0282513 | A1 | 10/2015 | Cook et al. |
| 2016/0050959 | A1* | 2/2016 | Vallini ................. A61K 31/221 |
| | | | 426/74 |
| 2017/0000181 | A1 | 1/2017 | Erdmann et al. |
| 2017/0028005 | A1 | 2/2017 | Turner |
| 2017/0127702 | A1 | 5/2017 | Hansen et al. |
| 2018/0168215 | A1 | 6/2018 | Kuang et al. |
| 2018/0235259 | A1 | 8/2018 | Jia et al. |
| 2019/0175703 | A1 | 6/2019 | Kasarle et al. |
| 2020/0367542 | A1 | 11/2020 | Hentschel et al. |

FOREIGN PATENT DOCUMENTS

| | | |
|---|---|---|
| CN | 108175006 | 6/2018 |
| CN | 109156817 | 1/2019 |
| CN | 109619570 | 4/2019 |
| DE | 3935906 | 5/1991 |
| EP | 0404964 | 1/1991 |
| EP | 1559703 | 12/2008 |
| EP | 2606747 | 12/2011 |
| EP | 2718418 | 8/2015 |
| JP | H-11332514 | 12/1999 |
| JP | 2017093428 | 6/2017 |
| JP | 2020000213 | 1/2020 |
| KR | 20170029080 | 3/2017 |
| KR | 101814442 | 1/2018 |
| KR | 101971671 | 4/2019 |
| RU | 2586742 C2 | 6/2016 |
| WO | WO-99/59564 | 11/1999 |
| WO | WO-02087544 | 11/2002 |
| WO | WO-2008/057968 | 5/2008 |
| WO | WO-2013076121 | 5/2013 |
| WO | WO-2015/138916 | 9/2015 |
| WO | WO-2016/020486 | 2/2016 |
| WO | WO-2016/020488 | 2/2016 |
| WO | WO-2016157868 | 10/2016 |

OTHER PUBLICATIONS

Pintaudi et al, Int. J. Endocrinology, 2016, pp. 1-4.*
Yu et al, J. Clinical Immun. 2012, 32. 1360-1371.*
Croze et al, J. Nutritional Biochemistry, 2013, 24, 457-466.*
Ruiz-Aceituno et al, Journal of the Science of Food and Agriculture, 2013, 2797-2803.*
Croze et al, Journal of Nutritional Biochemistry, 2013, 24, 457-466.*
Yoo et al, Nutrients, 2017, 9(1), 1-12; published Dec. 26, 2016.*
Zhong et al. Thermal Cycling Cascade Biocatalysis of myo-Inositol Synthesis from Sucrose. ACS Catal. 2017, 7, 5992-5999. Published: Jul. 25, 2017. (Year: 2017).*
Pintaudi, et al., "The Effectiveness of Myo-Inositol Treatment in Type 2 Diabetes", 2016, 5 pages, vol. 2016, International Journal of Endocrinology.
Sardi, B., "The FDA-Approved Anti-Diabetic Drug You Can Buy By The Pound (And It Was Stolen From Nature)", 2013, 3 pages, Beyond Vaccines.
Belloir, et al., "Sweeteners and sweetness enhancers", Jul. 2017, pp. 279-285, vol. 20, No. 4, Current Opinion in Clinical Nutrition & Metabolic Care.
International Search Report and Written Opinion dated Nov. 21, 2018 in International Application No. PCT/US2018/49965.
Ruiz-Aceituno, Laura, et al. "Optimisation of a Biotechnological Procedure for Selective Fractionation of Bioactive Inositols in Edible Legume Extracts." Journal of the Science of Food and Agriculture, vol. 93, No. 11, 2013, pp. 2797-2803., doi:10.1002/jsfa.6103.
Troyano, et al, "Monosaccharides and myo-Inositol in Commerical Milks", 1996, pp. 815-817, vol. 44, J. Agric. Food Chem.
Dyck, et al, "Nerve Glucose, Fructose, Sorbitol, myo-Inositol, and Fiber Degeneration and Regeneration in Diabetic Neuropathy", Sep. 1, 1988, pp. 542-548, vol. 319, No. 9, The New England Journal of Medicine.
Lee, et al, "Quantitative Study of Free Sugars and Myo-Inositol in Citrus Juices by HPLC and Literature Compilation", Feb. 6, 2007, pp. 2123-2141, vol. 23, No. 14, Journal of Liquid Chromatography & Related Technologies.
Hoffmann-Ostenhof, et al, "The biosynthesis of myo-inositol and its isomers", 1982, pp. 1863-1871, vol. 60, Can. J. Chem.
Eisenberg, et al, "[11] Measurement of Biosynthesis of myo-Inositol from Glucose 6-Phosphate", 1987, pp. 127-143, vol. 141, Methods In Enzymology.
Fujisawa, et al, "An In Virto Enzyme System for the Production of myo-Inositol from Starch", Aug. 2017, pp. 1-14, vol. 83, No. 16, Applied and Environmental Microbiology.
Extended European Search Report dated Mar. 16, 2021 in European Application No. 18855104.8.
Korban, et al, "Compsn. For diluting cryo-preserved boar sperm-contains supplementary fructose, inositol, magnesium sulphate and calcium chloride to increase mobility, survival and fertilizing power", Nov. 15, 1985, vol. 1986, No. 22, WPI/Thomson, XP002636583.
Muscogiuri Giovanna, et al, "Inositols in the Treatment of Insulin-Mediated Diseases", Jan. 1, 2016, vol. 2016, pp. 1-6, International Journal of Endocrinology, XP55781579.
EPO Examination Report ("Communication Pursuant to Article 94(3) EPC") Issued in corresponding European Patent Application No. 18 855 104.8, dated Nov. 18, 2021.
Russian Office Action for RU 2020106615 dated Feb. 10, 2022.
Croze, et al., "Potential role and therapeutic interests of myo-inositol in metabolic diseases" Biochimie. (May 11, 2013), vol. 95, No. 10, pp. 811-1827.
Yu et al., "D-chiro-inositol Negatively Regulates the Formation of Multinucleated Osteoclasts by Down-Regulating NFATc1", J Clin Immunol. (Jun. 19, 2012), vol. 32, No. 6, pp. 1360-1371.
Rosas-Villegas, et al., "Differential Effect of Sucrose and Fructose in Combination with a High Fat Diet on Intestinal Microbiota and Kidney Oxidative Stress", Nutrients. (Apr. 16, 2017, vol. 9, No. 393, pp. 1-13.
Kierstein, et al., "Sugar Consumption Increases Susceptibility to Allergic Airway Inflammation and Activates the Innate Immune System in the Lung", J Allergy Clin Immunol, (Feb. 1, 2008), vol. 121, Iss. 2, suppl. 1, abstract only.
Chiou, et al., "Pharmaceutical Applications of Solid Dispersion Systems", Journal of Pharmaceutical Sciences, (Sep. 1971), vol. 60, No. 9, pp. 1281-1302.
Yeung, et al., "Hot-melt extrusion of sugar-starch-pellets" International Journal of Pharmaceutics, (Aug. 3, 2015), vol. 493 (1-2), pp. 390-403.
Stringer, "Drug", Encyclopedia Britannica, https://www.britannica.com, (Jun. 24, 2015) https://web.archive.org/web/20150624085903/http://www.britannica.com/science/drug-chemical-agent.
Who, "The Pursuit of Responsible Use of Medicines", Sharing and Learning from Country Experiences, (Oct. 2, 2012), pp. 1-78.

(56) References Cited

OTHER PUBLICATIONS

Kearny, et al., "Calcium and Vitamin D Supplementation by Outpatient Allergy Patients" J Allergy Clin Immunol, , (Feb. 2008), S196, Abstracts.
Examination Report dated Jun. 2, 2023 in corresponding European Patent Application No. 18855104.8.
Examination Report dated Aug. 14, 2023 in corresponding Chinese Patent Application No. 2018800423680.

* cited by examiner

LOW GLYCEMIC SUGAR COMPOSITION

FIELD OF THE INVENTION

The present disclosure relates generally to a low glycemic sugar and in particular, a composition comprising inositol and a sugar source such as but not limited to sucrose.

BACKGROUND OF THE INVENTION

Excessive sugar consumption is the leading cause of many modern diseases such as Alzheimer's disease, cancer, cardiovascular disease, diabetes, metabolic syndrome, and obesity. It is scientific theory that the consumption of sugar initiates these diseases by triggering inflammation cascades, in particular TNF-α. Therefore, it is understood that sugar (including but not limited to sucrose and glucose) is not toxic but the human body perceives it as such and in turn responds to protect itself by initiating pro-inflammatory responses in an attempt at mitigating a biological threat. This in turn causes a chronic state of inflammation and cytokine signaling that brings the onset of so many diseases.

SUMMARY OF THE INVENTION

The present invention is directed to a composition comprising sugar, such as, but not limited to sucrose, plus a chaperone molecule, e.g. inositol. The resulting composition, in an advantageous form prevents or limits the signaling of TNF-α and associated pro-inflammatory cytokines. For example, the addition of inositol to sugar is believed to be advantageous based on inositol's insulin mimetic properties. Further, the addition of inositol to sugar is believed to prevent the pro-inflammatory response by blocking key pro-inflammatory signaling receptors. Inositol is a pseudo vitamin that has a perceived sweetness to that of 75% of glucose and is suitable for addition to sugar to provide anti-inflammatory without detracting from sucrose's usefulness as an universal sweetener.

In alternative forms, the sugar consistent can be one or more other sugars than just sucrose. Examples of sugars that can be included with a chaperone molecule such as inositol, include but are not limited to glucose, sucrose, sucrolose, tagatose, galactose, high fructose corn syrup, fructose, isoglucose, and rhamnose.

The present composition, e.g. sugar plus inositol, can be incorporated in products such as cakes, candies, chocolate, medicines, soda, beverages, breads, ice cream, sugar packets, etc.

In one advantageous form, inositol is present in the composition, with a sugar source, in a requisite amount, such that when consumed by an individual, prevents or limits the signaling of TNF-α and associated pro-inflammatory cytokines in that individual. Accordingly, such a composition which combines inositol and a sugar source, such as sucrose, or one or more other sugars mentioned in this disclosure including a composition consisting essential of inositol and the aforementioned sugar source, has the characteristics of limit the signaling of TNF-α and/or associated pro-inflammatory cytokines, when administered, ingested or giving to an individual and metabolized by the individual.

In another advantageous form, inositol is present in the composition, with a sugar source in a requisite amount, such that when consumed by an individual, treats or limits the occurrence of obesity, diabetes, cancer, metabolic syndrome and neurological diseases. Accordingly, such a composition which combines inositol and a sugar source, such as sucrose, or one or more other sugars mentioned in this disclosure including a composition consisting essential of inositol and the aforementioned sugar source, has the characteristics of treating or limiting the occurrence of obesity, diabetes, cancer, metabolic syndrome and neurological diseases, when administered, ingested or giving to an individual and metabolized by the individual.

In yet another advantageous form, inositol is present in the composition in a requisite amount, such that when consumed by an individual, treats or limits depression associated with pro-inflammatory conditions such as intracranial myo-inositol depletion in prefrontal cortex and amygdala. Such a composition which combines inositol and a sugar source, such as sucrose, or one or more other sugars mentioned in this disclosure including a composition consisting essential of inositol and the aforementioned sugar source, has the characteristics of treating or limiting the occurrence of conditions such as intracranial myo-inositol depletion in prefrontal cortex and amygdala.

In still another advantageous form, inositol is present in the composition, with a sugar source, in a requisite amount, such that the composition consisting essentially of inositol and a sugar source has low glycemic properties.

In still yet another advantageous form, inositol is present in the composition, with a sugar source, in a requisite amount, such that when consumed by a female individual, fights PCOS (Polycystic Ovary Syndrome) in the female individual due to inositol having a synergistic mitigating effect on androgenic compounds produced as a result of chromic pro-inflammatory response to heightened glycemic impact on the endocrine system. Accordingly, such a composition which combines inositol and a sugar source, such as sucrose, or one or more other sugars mentioned in this disclosure including a composition consisting essential of inositol and the aforementioned sugar source, has the synergistic mitigating effect on androgenic compounds produced as a result of a chromic pro-inflammatory response to heightened glycemic impact on the endocrine system.

In another advantageous form, inositol is present in the composition, with a sugar source, in a requisite amount to limit Neural Tube Birth Defects caused due to chronic pre-natal pro-inflammation from to excessive sugar consumption when consumed by a female individual. Accordingly, such a composition which combines inositol and a sugar source, such as sucrose, or one or more other sugars mentioned in this disclosure including a composition consisting essential of inositol and the aforementioned sugar source, has characteristics, of limiting Neural Tube Birth Defects caused due to chronic pre-natal pro-inflammation from to excessive sugar consumption by the female individual.

In still another advantageous form, inositol is present in the composition in a requisite amount to improve fertility when administered to females by improving hormone responses, ovarian function, oocyte production and ovation rates. Accordingly, such a composition which combines inositol and a sugar source, such as sucrose, or one or more other sugars mentioned in this disclosure including a composition consisting essential of inositol and the aforementioned sugar source, has characteristics, of improving fertility when administered to females by improving hormone responses, ovarian function, oocyte production and ovation rates. This effect is believed to be based on reducing sugar induced chronic inflammation by inositol supplementation via the present composition consisting essentially of inositol and a sugar source, leading to limiting degenerated or/and immature oocytes.

In another advantageous form, inositol is present in the composition in a requisite amount with a sugar source, such that when administered to infants, limits the occurrence of neo-natal respiratory distress syndrome in such infants, such as premature or at-risk infants. Accordingly, such a composition which combines inositol and a sugar source, such as sucrose, or one or more other sugars mentioned in this disclosure including a composition consisting essential of inositol and the aforementioned sugar source has the characteristic of limiting the occurrence of neo-natal respiratory distress syndrome in such infants, such as premature or at-risk infants, when giving to such infants.

In still another advantageous form, inositol is present in the composition in a requisite amount with a sugar source, such that when administered to female individuals limits development of gestational diabetes during pregnancy caused by chronic pre-natal pro-inflammation due to excessive sugar consumption or hyper sensitivity of pro-inflammation signal receptors. Accordingly, such a composition which combines inositol and a sugar source, such as sucrose, or one or more other sugars mentioned in this disclosure including a composition consisting essential of inositol and the aforementioned sugar source has the characteristic of limiting the occurrence development of gestational diabetes during pregnancy caused by chronic pre-natal pro-inflammation due to excessive sugar consumption or hyper sensitivity of pro-inflammation signal receptors, when giving to females in need of treatment, therefrom.

In still another advantageous form, inositol is present in the composition in a requisite amount with a sugar source, such that when administered to female individuals mitigates negative neurological and psychological effects of PMS (Premenstrual Syndrome) due to hormonal depletion of intracranial depletion of myo-inositol. Accordingly, such a composition which combines inositol and a sugar source, such as sucrose, or one or more other sugars mentioned in this disclosure including a composition consisting essential of inositol and the aforementioned sugar source has the characteristic of mitigating negative neurological and psychological effects of PMS (Premenstrual Syndrome) due to hormonal depletion of intracranial depletion of myo-inositol, when giving to females in need of treatment, therefrom.

The aforementioned composition(s) consisting of inositol and a sugar source may include other components which do not alter the aforementioned properties and/or characteristics. Additional components include but are not limited to pharmaceutical carriers, binders, inert material and anti-clumping/anticaking agents, including but not limited to cellulose, calcium silicate, sodium aluminosilicate, sodium ferrocyanide, potassium ferrocyanide, calcium carbonate, and magnesium carbonate.

In addition, the present composition of inositol and a sugar source can be giving to individuals to treat or limit the occurrence of the aforementioned conditions, including the various methods discussed below.

In accordance with one aspect of the present invention, a method for treating or limiting the signaling of TNF-α and associated pro-inflammatory cytokines in an individual comprises administering a therapeutically effective amount of a composition comprising inositol and a sugar source, in a requisite amount, to an individual in need thereof, to thereby limit the signaling of TNF-α and associated pro-inflammatory cytokines in that individual.

In accordance with one aspect of the present invention, a method for treating or limiting the occurrence of obesity, diabetes, cancer, metabolic syndrome and neurological diseases comprises administering a therapeutically effective amount of a composition consisting essentially of inositol and a sugar source, in a requisite amount, to an individual in need thereof, to thereby limit the occurrence of obesity, diabetes, cancer, metabolic syndrome and neurological diseases.

In accordance with one aspect of the present invention, a method for treating or limiting depression associated with pro-inflammatory conditions such as intracranial myo-inositol depletion in prefrontal cortex and amygdala comprises administering a therapeutically effective amount of a composition comprising inositol and a sugar source, in a requisite amount, to an individual in need thereof, to thereby limit depression associated with pro-inflammatory conditions such as intracranial myo-inositol depletion in prefrontal cortex and amygdala.

In accordance with one aspect of the present invention, a method for treating or limiting PCOS (Polycystic Ovary Syndrome) in a female individual comprises administering a therapeutically effective amount of a composition comprising inositol and a sugar source, in a requisite amount, to a female individual in need thereof, to thereby limit an effect on androgenic compounds produced as a result of chromic pro-inflammatory response to heightened glycemic impact on the endocrine system.

In accordance with one aspect of the present invention, a method for treating or limiting Neural Tube Birth Defects comprises administering a therapeutically effective amount of a composition comprising inositol and a sugar source, in a requisite amount, to a female individual in need thereof, to thereby limit Neural Tube Birth Defects caused due to chronic pre-natal pro-inflammation from to excessive sugar consumption by the individual.

In accordance with one aspect of the present invention, a method for improving fertility in a female comprises administering a therapeutically effective amount of a composition comprising inositol and a sugar source, in a requisite amount, to a female individual in need thereof, to thereby improve hormone responses, ovarian function, oocyte production and ovation rates.

In accordance with another aspect of the present invention, a method for limiting the occurrence of neo-natal respiratory distress syndrome in such infants, comprises administering a therapeutically effective amount of a composition comprising inositol and a sugar source, in a requisite amount, to an infant in need thereof, to thereby limit the occurrence of neo-natal respiratory distress syndrome in such infants.

In accordance with still another aspect of the present invention, a method for treating or limiting development of gestational diabetes during pregnancy caused by chronic pre-natal pro-inflammation due to excessive sugar consumption or hyper sensitivity of pro-inflammation signal receptors comprises administering a therapeutically effective amount of a composition comprising inositol and a sugar source, in a requisite amount, to a female individual in need thereof, to thereby treat or limit development of gestational diabetes during pregnancy caused by chronic pre-natal pro-inflammation due to excessive sugar consumption or hyper sensitivity of pro-inflammation signal receptors.

In accordance with one aspect of the present invention, a method for limiting negative neurological and psychological effects of PMS (Premenstrual Syndrome) due to hormonal depletion of intracranial depletion of myo-inositol comprises administering a therapeutically effective amount of a composition comprising inositol and a sugar source, in a requisite amount, to a female individual in need thereof, to thereby limit negative neurological and psychological effects of PMS (Premenstrual Syndrome) due to hormonal depletion of intracranial depletion of myo-inositol in that individual.

The aforementioned methods for treating various individuals by administering a therapeutically effective amount of a composition comprising inositol and a sugar source does not further include a protein, lipid or another therapeutic agent, e.g. a drug or composition directed to treating the respective disease condition.

The present inventor discovered that surprisingly and unexpectedly, a composition have only a sugar source and inositol has the aforementioned properties. Prior to this discovery, one believed that other therapeutic agents were needed in addition to inositol in order to have the disclosed therapeutic properties and/or effects.

DETAILED DESCRIPTION

As used herein, the following terms and phrases shall have the meaning set forth below.

The phrase "naturally occurring" when referring to a compound means a compound that is in a form in which it can be found naturally. A compound is not in a form that is naturally occurring if, for example, the compound has been purified and separated from at least some of the other molecules that are found with the compound in nature. A "naturally occurring compound" refers to a compound that can be found in nature, i.e., a compound that has not been created or modified by man.

"Consisting essential of" with regard the present composition includes the specific consistent described and disclosed and any other ingredients or constituents that do not materially alter the therapeutic characteristics, properties and/or effects of the present composition (e.g. a sugar source and inositol). Other ingredients which do not materially affect the disclosed therapeutic characteristics, properties and/or effects of the present composition include but are not limited to binders, carriers, inherit material, and anticaking/anti-clumping agents.

"Treating" a condition or disease refers to curing as well as ameliorating at least one symptom of the condition or disease and limiting the occurrence of the condition or disease.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the patient and disease or condition being treated, the weight and age of the patient, the severity of the disease or condition, the manner of administration and the like, which can readily be determined by one or ordinary skill in the art. For example, certain compositions described herein may be administered in a sufficient amount to produce a desired effect at a reasonable benefit/risk ratio applicable to such treatment.

EXAMPLES

Example 1

A composition consisting of 70% sucrose and approximately 30% inositol.

Examples 2a-2d

Compositions consisting of sucrose/inositol with the following ratios:
a.) 50/50
b.) 60/40,
c.) 80/20 and
d.) 90/10.

Example 3

The process for manufacturing the compositions of Examples 1 and 2a-2d includes combining inositol with sucrose in the requisite amounts both in solid, crystalline form.

Example 4

The process for manufacturing the compositions of Examples 1 and 2a-2d includes heating sucrose to its melting point and heating inositol to its melting point. Next the inositol is added to the melted sucrose to form a combined sucrose/inositol molten slurry. The slurry is allowed to dry. Finally the dried product is passed through a blender or crushing device to reduce the resulting product in size and consistency of typical sugar product.

Example 5

The process for manufacturing the compositions of Examples 1 and 2a-2d includes adding the requisite amount of inositol during an actual initial manufacturing process of sucrose itself. Such initial sucrose manufacturing include conventional processes know to those of ordinary skill in the art. Accordingly, there are several opportune times during conventional sucrose manufacturing processes that allow inositol to be added.

For the purposes of promoting an understanding of the principles of the invention, the invention has been explained in relation to various embodiments, it is to be understood that various modifications thereof will be apparent to those skilled in the art upon reading the specification. The features of the various embodiments of the articles described herein may be combined within an article. Therefore, it is to be understood that the invention described herein is intended to cover such modifications as fall within the scope of the appended claims.

The invention claimed is:

1. A dry composition consisting of an effective amount of a sugar and myo-inositol wherein the sugar is selected from one or more of sucrose, a fructose, isoglucose, and galactose; and the dry composition mitigates the TNF-α response to the sugar.

2. The dry composition of claim 1, wherein the sugar is sucrose.

3. The dry composition of claim 1, wherein the sugar is fructose or galactose.

4. The dry composition of claim 3, wherein the sugar is present in around 70% by weight and the myo-inositol is present in approximately 30% by weight.

5. The dry composition of claim 3, wherein the sugar is present in around 50% by weight.

6. A dry composition consisting essentially of an effective amount of a sugar and myo-inositol with anti-TNF-α effects when administered to a patient in need of the anti-TNF-α effect, wherein the dry composition mitigates a TNF-α response to the sugar.

7. The dry composition of claim 6, wherein the sugar is sucrose.

8. The dry composition of claim 6, wherein the sugar is one or more sucrose, sucralose, fructose, isoglucose, and galactose.

9. The dry composition of claim 6, wherein the sugar is present in around 70% by weight and the myo-inositol is present in approximately 30% by weight.

10. The dry composition of claim 6, wherein the sugar is present in around 50% by weight.

11. A method of reducing or limiting the occurrence of diabetes, said method comprising administering a therapeutically effective amount of a dry composition of claim 6 to an individual in need thereof to thereby reduce or limit the occurrence of diabetes by mitigating effects of TNF-α.

12. The method of claim 11, wherein the dry composition does not include a lipid, protein or another anti-diabetes therapeutic agent.

13. A method of reducing or limiting the occurrence of inflammatory disease or conditions, said method comprising administering a therapeutically effective amount of a dry composition of claim 6 to an individual in need thereof to thereby reduce or limit the occurrence of an inflammatory disease or conditions by mitigating effects of TNF-α.

14. The method of claim 13, wherein the disease or condition is selected from the group consisting of PCOS (Polycystic Ovary Syndrome), neo-natal respiratory distress syndrome neural tube birth defects, obesity, diabetes, cancer, metabolic syndrome and neurological diseases or conditions induced by the signaling of TNF-α and pro-inflammatory cytokines.

15. The dry composition of claim 2, wherein a weight ratio of sucrose to myo-inositol is 50:50.

16. The dry composition of claim 2, wherein a weight ratio of sucrose to myo-inositol is 60:40.

17. The dry composition of claim 2, wherein a weight ratio of sucrose to myo-inositol is 70:30.

18. The dry composition of claim 2, wherein a weight ratio of sucrose to myo-inositol is 80:20.

19. The dry composition of claim 2, wherein a weight ratio of sucrose to myo-inositol is 90:10.

20. The method of claim 14, wherein the disease or condition is metabolic syndrome.

21. The method of claim 14, wherein the disease or condition is diabetes.

22. The dry composition of claim 1, wherein the sugar is fructose.

23. The dry composition of claim 1, wherein the sugar is isoglucose.

24. The dry composition of claim 22, wherein fructose is present in around 70% by weight and myo-inositol is present in approximately 30% by weight.

25. The dry composition of claim 22, wherein fructose is present in around 90% by weight and myo-inositol is present in approximately 10% by weight.

26. The dry composition of claim 2, wherein sucrose is present in around 70% by weight and myo-inositol is present in approximately 30% by weight.

* * * * *